(12) United States Patent
Pudil et al.

(10) Patent No.: US 12,397,093 B2
(45) Date of Patent: Aug. 26, 2025

(54) SORBENT CARTRIDGE DESIGNS

(71) Applicant: MOZARC MEDICAL US LLC, Minneapolis, MN (US)

(72) Inventors: Bryant J. Pudil, Plymouth, MN (US); Mark David Schneider, Mound, MN (US); Michael J Elvidge, Minneapolis, MN (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 287 days.

(21) Appl. No.: 17/323,081

(22) Filed: May 18, 2021

(65) Prior Publication Data
US 2022/0370696 A1  Nov. 24, 2022

(51) Int. Cl.

| | |
|---|---|
| *A61M 1/16* | (2006.01) |
| *A61M 39/10* | (2006.01) |
| *B01D 15/18* | (2006.01) |
| *B01D 15/22* | (2006.01) |
| *B01J 20/02* | (2006.01) |
| *B01J 20/06* | (2006.01) |
| *B01J 20/08* | (2006.01) |
| *B01J 20/20* | (2006.01) |
| *B01J 20/24* | (2006.01) |
| *B01J 20/28* | (2006.01) |
| *B01J 39/12* | (2006.01) |
| *B01J 41/10* | (2006.01) |

(52) U.S. Cl.
CPC ........ *A61M 1/1609* (2014.02); *A61M 1/1656* (2013.01); *A61M 39/10* (2013.01); *B01D 15/18* (2013.01); *B01D 15/22* (2013.01); *B01J 20/0211* (2013.01); *B01J 20/06* (2013.01); *B01J 20/08* (2013.01); *B01J 20/20* (2013.01); *B01J 20/24* (2013.01); *B01J 20/28045* (2013.01); *B01J 39/12* (2013.01); *B01J 41/10* (2013.01); *A61M 2205/3334* (2013.01); *B01J 2220/62* (2013.01)

(58) Field of Classification Search
None
See application file for complete search history.

(56) References Cited

U.S. PATENT DOCUMENTS

| | | | |
|---|---|---|---|
| 1,617,288 | A | 2/1927 | Kenney |
| 2,703,313 | A | 3/1955 | Gill |
| 3,608,729 | A | 9/1971 | Haselden |
| 3,617,545 | A | 11/1971 | Dubois |
| 3,617,558 | A | 11/1971 | Jones |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

European Search Report for App. No. 15812081.6, dated Mar. 8, 2018.

(Continued)

*Primary Examiner* — Hayden Brewster

(57) ABSTRACT

Sorbent cartridges having a flow control insert to improve the functional capacity of a sorbent cartridge is provided. Flow control inserts can include a plurality of flow channels filled with sorbent material through which fluid to be regenerated can travel in the sorbent cartridge.

20 Claims, 16 Drawing Sheets

(56) References Cited

U.S. PATENT DOCUMENTS

| | | |
|---|---|---|
| 3,669,878 A | 6/1972 | Marantz |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,060,485 A | 11/1977 | Eaton |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,206,054 A | 6/1980 | Moore |
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,661,246 A | 4/1987 | Ash |
| 4,678,408 A | 7/1987 | Mason |
| 4,684,460 A | 8/1987 | Issautier |
| 4,685,903 A | 8/1987 | Cable |
| 4,687,582 A | 8/1987 | Dixon |
| 4,750,494 A | 6/1988 | King |
| 4,765,907 A | 8/1988 | Scott |
| 4,826,663 A | 5/1989 | Alberti |
| 4,828,693 A | 5/1989 | Lindsay |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,491,993 B1 | 12/2002 | Forbes |
| 6,521,184 B1 | 2/2003 | Edgson et al. |
| 6,554,798 B1 | 4/2003 | Mann |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Waguespack et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,276,042 B2 | 10/2007 | Polaschegg |
| 7,309,323 B2 | 12/2007 | Gura |
| 7,318,892 B2 | 1/2008 | Connell |
| 7,326,576 B2 | 2/2008 | Womble et al. |
| 7,384,543 B2 | 6/2008 | Jonsson et al. |
| 7,435,342 B2 | 10/2008 | Tsukamoto |
| 7,462,161 B2 | 12/2008 | O'Mahony et al. |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | Mccombie |
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers |
| 7,776,210 B2 | 8/2010 | Rosenbaum |
| 7,794,141 B2 | 9/2010 | Perry |
| 7,794,419 B2 | 9/2010 | Paolini |
| 7,850,635 B2 | 12/2010 | Polaschegg |
| 7,867,214 B2 | 1/2011 | Childers |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |
| 7,955,290 B2 | 6/2011 | Karoor |
| 7,967,022 B2 | 6/2011 | Grant |

(56) References Cited

U.S. PATENT DOCUMENTS

| | | |
|---|---|---|
| 7,981,082 B2 | 7/2011 | Wang |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,182,673 B2 | 5/2012 | Childers et al. |
| 8,183,046 B2 | 5/2012 | Lu |
| 8,187,250 B2 | 5/2012 | Roberts |
| 8,197,439 B2 | 6/2012 | Wang |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 10,695,481 B2 | 6/2020 | Kelly et al. |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2004/0257409 A1 | 12/2004 | Cheok |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0126998 A1 | 6/2005 | Childers |
| 2005/0131332 A1 | 6/2005 | Kelly |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0157413 A1 | 7/2006 | Bene |
| 2006/0189926 A1 | 8/2006 | Hall et al. |
| 2006/0195064 A1 | 8/2006 | Plahey |
| 2006/0196157 A1* | 9/2006 | Greer .................... A62B 23/02 55/500 |
| 2006/0217771 A1 | 9/2006 | Soykan |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0012864 A1 | 1/2009 | Goldberg |
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant et al. |
| 2010/0051552 A1 | 3/2010 | Rohde |
| 2010/0076364 A1 | 3/2010 | O'Mahony et al. |
| 2010/0078381 A1 | 4/2010 | Merchant |
| 2010/0078387 A1 | 4/2010 | Wong |

(56) References Cited

U.S. PATENT DOCUMENTS

| | | |
|---|---|---|
| 2010/0084330 A1 | 4/2010 | Wong |
| 2010/0094158 A1 | 4/2010 | Solem |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114001 A1 | 5/2010 | O'Mahony |
| 2010/0114012 A1 | 5/2010 | Sandford |
| 2010/0137693 A1 | 6/2010 | Porras |
| 2010/0168546 A1 | 7/2010 | Kamath |
| 2010/0168641 A1 | 7/2010 | O'Mahony et al. |
| 2010/0213127 A1 | 8/2010 | Castellarnau |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0228516 A1 | 9/2013 | Jonsson |
| 2013/0274642 A1 | 10/2013 | Soykan et al. |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0135942 A1* | 5/2016 | Drager ............... A61F 2/0036 600/30 |
| 2016/0236188 A1 | 8/2016 | Menon |
| 2016/0243540 A1 | 8/2016 | Menon |
| 2016/0243541 A1 | 8/2016 | Menon |
| 2017/0189598 A1* | 7/2017 | Slade ............... B01J 20/28052 |

FOREIGN PATENT DOCUMENTS

| | | |
|---|---|---|
| CN | 103402563 A | 11/2013 |
| CN | 104936633 | 9/2015 |
| CN | 105658326 A | 6/2016 |
| DE | 3110128 A1 | 9/1982 |
| DE | 102011052188 | 1/2013 |
| EP | 0266795 A2 | 11/1987 |
| EP | 0264695 | 4/1988 |
| EP | 0614081 A1 | 10/1993 |
| EP | 1085295 | 11/2001 |
| EP | 711182 B1 | 6/2003 |
| EP | 1364666 A1 | 11/2003 |
| EP | 0906768 B1 | 2/2004 |
| EP | 1701752 A2 | 9/2006 |
| EP | 1450879 | 10/2008 |
| EP | 1991289 | 11/2008 |
| EP | 1592494 B1 | 6/2009 |

(56) References Cited

FOREIGN PATENT DOCUMENTS

| | | |
|---|---|---|
| EP | 2100553 A1 | 9/2009 |
| EP | 2575827 A2 | 12/2010 |
| EP | 2576453 A2 | 12/2011 |
| EP | 2446908 | 5/2012 |
| EP | 2701580 | 11/2012 |
| EP | 2701595 | 11/2012 |
| EP | 1545652 B1 | 1/2013 |
| EP | 1684625 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |
| EP | 1345687 | 6/2013 |
| EP | 2701596 | 3/2014 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 200744602 | 2/2007 |
| JP | 200744602 A | 2/2007 |
| JP | 5-99464 | 10/2012 |
| JP | 2013502987 | 10/2013 |
| WO | 9106326 A1 | 5/1991 |
| WO | 9532010 A1 | 11/1995 |
| WO | 9937342 | 7/1999 |
| WO | 2000038591 A2 | 7/2000 |
| WO | 0057935 | 10/2000 |
| WO | 200066197 A1 | 11/2000 |
| WO | 200170307 A1 | 9/2001 |
| WO | 2001085295 A2 | 9/2001 |
| WO | 0185295 A2 | 11/2001 |
| WO | 2002043859 | 6/2002 |
| WO | 2003043677 A2 | 5/2003 |
| WO | 2003043680 | 5/2003 |
| WO | WO 2003041764 | 5/2003 |
| WO | 2003051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | WO 2005/062973 A3 | 7/2005 |
| WO | 2005123230 | 12/2005 |
| WO | 2007089855 A2 | 8/2007 |
| WO | WO 20070103411 | 9/2007 |
| WO | 2008075951 A1 | 6/2008 |
| WO | 2009026603 | 12/2008 |
| WO | 2009064984 | 5/2009 |
| WO | 2009157877 A1 | 12/2009 |
| WO | 2009157878 A1 | 12/2009 |
| WO | 20090157877 | 12/2009 |
| WO | 2010028860 | 3/2010 |
| WO | 2010102190 A4 | 11/2010 |
| WO | 2010141949 | 12/2010 |
| WO | WO 2011/017215 | 2/2011 |
| WO | 2011025705 A1 | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 | 2/2013 |
| WO | 2013019994 A2 | 2/2013 |
| WO | 2013022024 A1 | 2/2013 |
| WO | 2013022837 A1 | 2/2013 |
| WO | 2013025844 | 2/2013 |
| WO | 2013027214 | 2/2013 |
| WO | 2013028809 | 2/2013 |
| WO | WO 2013-025957 | 2/2013 |
| WO | WO2014121238 A1 | 2/2013 |
| WO | 2013030642 A1 | 3/2013 |
| WO | 2013030643 A1 | 3/2013 |
| WO | 2012060700 | 5/2013 |
| WO | 2012162515 A3 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2013114063 A1 | 8/2013 |
| WO | 2013121162 A1 | 8/2013 |
| WO | 14066254 | 5/2014 |
| WO | 14066255 | 5/2014 |
| WO | 14077082 | 5/2014 |
| WO | 2014121162 | 8/2014 |
| WO | 2014121163 | 8/2014 |
| WO | 2014121167 | 8/2014 |
| WO | 2014121169 | 8/2014 |
| WO | WO 2015/080895 | 4/2015 |
| WO | WO 2015060914 | 4/2015 |
| WO | WO 2015/126879 | 8/2015 |
| WO | 2015142624 | 9/2015 |
| WO | 2015199764 | 12/2015 |
| WO | WO 2015-199863 | 12/2015 |
| WO | WO 2015-199864 | 12/2015 |
| WO | WO 2015199765 | 12/2015 |
| WO | WO 2016/191039 | 12/2016 |

OTHER PUBLICATIONS

European Search Report for App. No. 18153940.4, Dated Jun. 12, 2018.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report in EP 15811454, dated Feb. 15, 2018.
European Search Report in EP 15812559.1, dated Jan. 31, 2018.
Office Action in Japanese Application No. 2016-553344, dated Apr. 24, 2018.
PCT/US2016/030304_IPRP.
PCT/US2016/030319_IPRP.
Search Report for Brazilian App. No. BR112016019111, dated Mar. 12, 2020.
Search Report for EP App. No. 17203984.4, dated Mar. 29, 2018.
Search Report in EP App. No. 15752771, Dated Nov. 22, 2017.
[NPL388] Daugirdas Jt. Second generation logarithmic estimates of single-pool variable vol. Kt/V and analysis of error. J Am Soc Nephrol, 1993: 4:1205-13.
[NPL389] Steil et al. Intl Journ Artif Organs, 1993, In Vivo Verification of an Automatic Noninvasive System for Real Time Kt Evaluation, Asaio J., 1993, 39:M348-52.
[NPL39] PCT/US2012/034332, International Search Report, Jul. 5, 2012.
[NPL3] PCT/US2015/019901 International Search Report and Written Opinion mailed Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL494] John Wm Agar: Review: Understanding sorbent dialysis systems, Nephrology, vol. 15, No. 4, Jun. 1, 2010, pp. 406-411.
[NPL499] EP. App. 14746193.3 Search Report dated Oct. 19, 2016.
[NPL4] PCT/US2015/016270 International Search Report and Written Opinion mailed Jun. 5, 2015.
[NPL518] Office Action in U.S. Appl. No. 14/269,589, Dated Nov. 4, 2016

(56) References Cited

OTHER PUBLICATIONS

[519] Office Action in U.S. Appl. No. 13/586,824 Dated Dec. 21, 2015.
[NPL532] Eureopean Search Report for App. No. EP14745643 Dated Oct. 6, 2016.
[NPL548] PCT/US15/18587 International Preliminary Report on Patentability Dated Jun. 6, 2016.
[NPL550] European Search Opinion for App. No. EP12826180 Dated Mar. 19, 2015.
[NPL551] European Search Opinion for App. No. 12826180 Dated Jan. 18, 2016.
[NPL552] Khanna, Ramesh, R.T. Krediet, and Karl D. Nolph. Nolph and Gokals Textbook of Peritoneal Dialysis New York: Springer 2009. Print.
[NPL553] Ruperez et al., Comparison of a tubular pulsatile pump and a volumetric pump for continuous venovenous renal replacement therapy in a pediatric animal model, 51 Asaio J. 372, 372-375 (2005).
[NPL554] St. Peter et al., Liver and kidney preservation by perfusion, 359 The Lancet 604, 606(2002).
[NPL555] Dasselaar et al., Measurement of relative blood vol. changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 Dated Jan. 11, 2016.
[NPL559] Office Action in U.S. Appl. No. 13/565,733 Dated Jun. 11, 2015.
[NPL561] Office Action in U.S. Appl. No. 13/757,792 Dated Jun. 2, 2016.
[NPL586] International Search Report from International Application No. PCT/US2014/014347 dated May 9, 2014.
[NPL590] PCT/US2016/030319 Written Opinion mailed Jul. 27, 2016.
[NPL591] PCT/US2016/030320 Written Opinion mailed Jul. 27, 2016.
[NPL596] PCT/US2012/014347, International Search Report.
[NPL5] PCT/US2015/016273 International Search Report and Written Opinion mailed Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 mailed Dec. 26, 2016.
[NPL603] Japanese Patent Publication No. S50-70281A.
[NPL605] PCT/US2015/032494 Written Opinion mailed Nov. 19, 2015.
[NPL606] PCT/US2015/032494 International Search Report mailed Nov. 19, 2015.
[NPL607] PCT/US2015/019901 International Preliminary Report on Patentability mailed May 27, 2016.
[NPL608] PCT/US2015/019901 Written Opinion mailed May 27, 2016.
[NPL609] PCT/US2015/019901 Written Opinion mailed Jun. 5, 2015.
[NPL610] PCT/US2015/019901 International Search Report mailed Jun. 5, 2015.
[NPL611] PCT/US2015/032485 International Preliminary Report on Patentability mailed May 11, 2016.
[NPL612] PCT/US2015/032485 International Preliminary Report on Patentability mailed May 11, 2016.
[NPL613] PCT/US20115/032485 International Preliminary Report on Patentability mailed May 11, 2016.
[NPL614] PCT/US2016/030304 International Search Report mailed Jul. 27, 2016.
[NPL615] PCT/US2016/030304 Written Opinion mailed Jul. 27, 2016.
[NPL616] PCT/US2016/030312 Written Opinion mailed Jul. 28, 2016.
[NPL617] PCT/US2016/030312 International Search Report mailed Jul. 28, 2016.
[NPL618] PCT/US2016/030319 International Search Report mailed Jul. 27, 2016.
[NPL619] PCT/US2016/030319 Written Opinion mailed Jul. 27, 2016.
[NPL620] PCT/US2016/030320 Written Opinion mailed Jul. 28, 2016.
[NPL621] PCT/US2016/030320 International Search Report mailed Jul. 28, 2016.
[NPL622] PCT/US2015/032485 Written Opinion mailed Oct. 16, 2015.
[NPL623] PCT/US2015/032485 Written Opinion mailed Oct. 16, 2016.
[NPL626] PCT/US2015/032485 International Search Report and Written Opinion mailed Oct. 16, 2015.
[NPL634] PCT/US2016/030320 International Preliminary Report on Patentability, mailed Apr. 20, 2017.
[NPL654] International Preliminary Report from International Application No. PCT/US2014/014348 dated Jan. 9, 2015.
[NPL655] European Search Report from European Application No. EP 14746193.3 dated Oct. 19, 2016.
[NPL656] European Search Report from European Application No. EP 14746193.3 dated Jun. 8, 2016.
[NPL657] PCT/US2014/014345 Written Opinion dated Jun. 24, 2015.
[NPL658] PCT/US2014/014345 International Search Report and Written Opinion dated May 30, 2014.
[NPL659] Office Action in European Application No. 14746428.03 dated Feb. 8, 2017.
[NPL660] European Search Report in European Application No. 14746428.03 dated Aug. 25, 2016.
[NPL661] PCT/US2014/014346 Writtent Opinion dated Apr. 10, 2015.
[NPL662] PCT/US2014/014346 International Search Report and Writtent Opinion dated May 23, 2014.
[NPL663] EP 14746415.0 European Search Report dated Aug. 22, 2016.
[NPL664] Office Action in European Application No. EP 14746415.0 dated Apr. 19, 2017.
[NPL670] Office Action in European Application No. 14746415.0 dated Apr. 19, 2017.
[NPL681] PCT/US2015/020047 International Search Report and Written Opinion mailed Jun. 29, 2015.
[NPL682] PCT/US2015/020047 International Preliminary Report on Patentability mailed Jun. 30, 2015.
[NPL684] PCT/US2015/020044 Written Opinion dated Jun. 21, 2016.
[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL690] US2015/019881 International Search Report and Written Opinion dated Jun. 29, 2015.
[NPL692] PCT/US2014/065950 International Preliminary Report on Patentability mailed Oct. 28, 2015.
[NPL696] PCT/US2015/032485 Written Opinion mailed May 9, 2016.
[NPL6] PCT/US2015/032492 Written Opinion mailed Nov. 19, 2015.
[NPL720] PCT/US2015/019901 International Search Report and Written Opinion mailed Jun. 5, 2015.
[NPL721] PCT/US2015/019901 International Preliminary Report on Patentability mailed May 27, 2016.
[NPL722] PCT/US2015/032494 International Preliminary Report on Patentablity mailed Dec. 27, 2016.

(56) References Cited

OTHER PUBLICATIONS

[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL736] Office Action in European Application No. 14746193.3 dated Apr. 19, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion mailed Jun. 29, 2015.
[NPL8] PCT/US2015/020044 International Search Report Written Opinion mailed Jun. 30, 2015.
[NPL90] Nedelkov, et. al., Design of buffer exchange surfaces and sensor chips for biosensor chip mass spectrometry, Proteomics, 2002, 441-446, 2(4).
[NPL] European Search Report App 14865374.4, Jun. 12, 2017.
Chinese Office Action for App. No. 201580034005.9, dated Dec. 12, 2018.
Chinese Office Action in App. No. 201580009563.X, dated Mar. 13, 2018.
[NPL105] Brynda, et. al., The detection of toman 2-microglebuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et al., Miniature urea sensor based on H(+)-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, Jul. 6, 2012.
[NPL147] PCT/US2012/034335, International Search Report, Sep. 5, 2012.
[NPL148] PCT/US/2012/034327, International Search Report, Aug. 13, 2013.
[NPL149] PCT/US/2012/034329, International Search Report, Dec. 3, 2012.
[NPL162] International Search Report from PCT/US2012/051946 mailed Mar. 4, 2013.
[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion mailed Mar. 9, 2015.
[NPL176] Bleyer, et. al., Sudden and cardiac death rated in hemodialysis patients, Kidney International. 1999, 1553-1559: 55.
[NPL187] PCT/US2012/034333, International Preliminary Report on Patentability, Oct. 29, 2013.
[NPL188] PCT/US2012/034333, International Search Report, Aug. 29, 2012.
[NPL1] PCT/US2014/065950 International Search Report and Written Opinion mailed Feb. 24, 2015.

[NPL205] Culleton, Bf et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL230] Redfield, et. al., Restoration of renal response to atria! natriuretic factor in experimental low-output heart failure, Am. J. Physiol., Oct. 1, 1989, R917-923:257.
[NPL231] Rogoza, et al., Validation of A&D UA-767 device for the self-measurement of blood pressure, Blood Pressure Monitoring, 2000, 227-231, 5(4).
[NPL234] Lima, et al., An electrochemical sensor based on nanostructure hollandite-type manganese oxide for detection of potassium ion, Sensors, Aug. 24, 2009, 6613-8625, 9.
[NPL235] Maclean, Et, Al., Effects of hindlimb contraction on pressor and muscle interstitial metabolite responses in the cat, J. App. Physiol., 1998, 1583-1592, 85(4).
[NPL246] PCT/US2014/014346 International Search Report and Written Opinion.
[NPL248] PCT/US2014/014345 International Search Report and Written Opinion, mailed May 2014.
[NPL264] PCT/US2014/014357 International Search Report and Written Opinion dated May 19, 2014.
[NPL264] PCT/US2014/014357 International Search Report and Written Opinion mailed May 19, 2014.
[NPL268] Ronco et al. 2008, Cardiorenal Syndrome, Journal American College Cardiology, 52:1527-1539, Abstract.
[NPL26] Overgaard, et al., Activity-induced recovery of excitability in K+-depressed rat soleus muscle, Am. J. P 280: R48-R55, Jan. 1, 2001.
[NPL27] Overgaard et al., Relations between excitability and contractility in rate soleusmuscle: role of the NA+-K+ pump and NA+-K—S gradients. Journal of Physiology, 1999, 215-225, 518(1).
[NPL2] PCT/US2015/032492 International Search Report mailed Nov. 19, 2015.
[NPL306] Coast, et al. 1990, An approach to Cardiac Arrhythmia analysis Using Hidden Markov Models, IEEE Transactions On Biomedical Engineering. 1990, 37(9):826-835.
[NPL32] Secemsky, et al., High prevalence of cardiac autonomic dysfunction and T-wave alternans in dialysis patients. Heart Rhythm, Apr. 2011, 592-598 : vol. 8, No. 4.
[NPL35] Wei, Et. Al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid Column World Acad. of Sci., Engineering & Tech., vol. 28, pp. 264-268, Published Jan. 1, 2007.
[NPL386] The FHN Trial Group. In-Center. Hemodialysis Six Times per Week versus Three Times per Week, New England Journal of Medicine, 2010 Abstract.
[NPL387] Gotch Fa, Sargent Ja A mechanistic analysis of the National Cooperative Dialysis Study (NCDS). Kidney int. 1985: 28:526-34.
U.S. Appl. No. 13/757,693, filed Feb. 1, 2013, Medtronic.
U.S. Appl. No. 13/757,709, filed Feb. 1, 2013, Medtronic.
U.S. Appl. No. 13/757,728, filed Feb. 1, 2013, Medtronic.
U.S. Appl. No. 13/757,538, filed Mar. 15, 2013, Medtronic.
U.S. Appl. No. 61/760,033, filed Feb. 1, 2013, Medtronic.

\* cited by examiner

SORBENT CARTRIDGE DESIGNS

FIELD

The disclosure relates to sorbent cartridges having a flow control insert to improve the functional capacity of the sorbent cartridge. The flow control insert can include a plurality of flow channels filled with sorbent material through which fluid to be regenerated can travel in the sorbent cartridge.

BACKGROUND

Sorbent-based multi-pass dialysis systems can reduce the volume of purified water needed for therapy. Sorbent cartridges operate by adsorbing ions and other waste solutes from spent dialysate, allowing the repurified to be reused. However, sorbent materials have a finite capacity. If the capacity of a sorbent cartridge is reached during treatment, treatment must be stopped. Due to channeling and non-uniform flow of dialysate through a sorbent cartridge, certain portions of the sorbent material may undergo greater ion exchange with the dialysate than others, increasing the rate at which the capacity of these portions of sorbent material is reached, which allows solutes intended to be removed by the sorbent cartridge to return to the dialyzer.

Hence, there is a need for systems and methods that can increase the adsorptive capacity of a sorbent cartridge, allowing full treatment of larger or more uremic patients without increasing the size requirements for the sorbent cartridge. There is a need for systems and methods that can improve flow distribution of dialysate through the sorbent cartridge, allowing more effective solute removal by the sorbent cartridge.

SUMMARY OF THE INVENTION

The problem to be solved is increasing the adsorptive capacity of a sorbent cartridge. The solution is to include a flow control insert within the sorbent cartridge to more efficiently distribute fluid flow throughout the sorbent material.

The first aspect relates to a sorbent cartridge. In any embodiment, the sorbent cartridge can include a sorbent cartridge casing; at least one sorbent material inside the sorbent casing; and a flow control insert; the flow control insert having a plurality of flow channels filled with the at least one sorbent material.

In any embodiment, the at least one sorbent material can include zirconium phosphate.

In any embodiment, the at least one sorbent material can include zirconium oxide.

In any embodiment, the at least one sorbent material can include at least one sorbent material selected from a group of activated carbon, alumina, urease, an anion exchange material, a cation exchange material, zirconium phosphate, and zirconium oxide.

In any embodiment, each of the plurality of flow channels can have a hexagonal shape.

In any embodiment, the plurality of flow channels can form a plurality of cylinders.

In any embodiment, the plurality of cylinders can be a plurality of concentric cylinders.

In any embodiment, the flow control insert can have a substantially flat top portion.

In any embodiment, the flow control insert can have a dome-shaped top portion.

In any embodiment, the sorbent cartridge can include a compression insert between a top portion of the flow control insert and an inner top of the sorbent cartridge casing.

In any embodiment, the flow control insert can contact the compression insert.

The features disclosed as being part of the first aspect can be in the first aspect, either alone or in combination, or follow any arrangement or permutation of any one or more of the described elements. Similarly, any features disclosed as being part of the first aspect can be in a second or third aspect described below, either alone or in combination, or follow any arrangement or permutation of any one or more of the described elements.

The second aspect relates to a flow control insert for a sorbent cartridge. In any embodiment, the flow control insert can include a plurality of flow channels; the flow control insert insertable into a sorbent cartridge containing at least one sorbent material.

In any embodiment, each of the plurality of flow channels can have a substantially hexagon shape.

In any embodiment, the plurality of flow channels can form a plurality of cylinders.

In any embodiment, the plurality of cylinders can be a plurality of concentric cylinders.

In any embodiment, the flow control insert can have a substantially flat top portion.

In any embodiment, the flow control insert can have a dome-shaped top portion.

In any embodiment, the flow control insert can be constructed from a material selected from: polypropylene, polyethylene, stainless steel, glass, plastic, or a combination thereof.

The features disclosed as being part of the second aspect can be in the second aspect, either alone or in combination, or follow any arrangement or permutation of any one or more of the described elements. Similarly, any features disclosed as being part of the second aspect can be in the first or third aspect, either alone or in combination, or follow any arrangement or permutation of any one or more of the described elements.

The third aspect is drawn to a dialysate flow path. In any embodiment, the dialysate flow path can include a first connector fluidly connectable to a dialyzer outlet; a second connector fluidly connectable to a dialyzer inlet; at least one dialysate pump; and at least a first sorbent module; the sorbent module including: a sorbent cartridge casing; at least one sorbent material inside the sorbent casing; and a flow control insert; the flow control insert having a plurality of flow channels filled with the at least one sorbent material.

In any embodiment, the dialysate flow path can include at least a second sorbent module; wherein the second sorbent module has a second sorbent cartridge casing; at least one sorbent material inside the second sorbent casing; and a second flow control insert; the second flow control insert having a plurality of flow channels filed with the at least one sorbent material.

In any embodiment, the first and second sorbent modules can contain different sorbent materials.

In any embodiment, the first sorbent module can contain at least one sorbent material selected from the group of: activated carbon, alumina, urease, zirconium phosphate, zirconium oxide, an anion exchange material, and a cation exchange material.

The features disclosed as being part of the third aspect can be in the third aspect, either alone or in combination, or follow any arrangement or permutation of any one or more of the described elements. Similarly, any features disclosed as being part of the third aspect can be in the first or second aspect, either alone or in combination, or follow any arrangement or permutation of any one or more of the described elements.

DETAILED DESCRIPTION

Figure 1A:
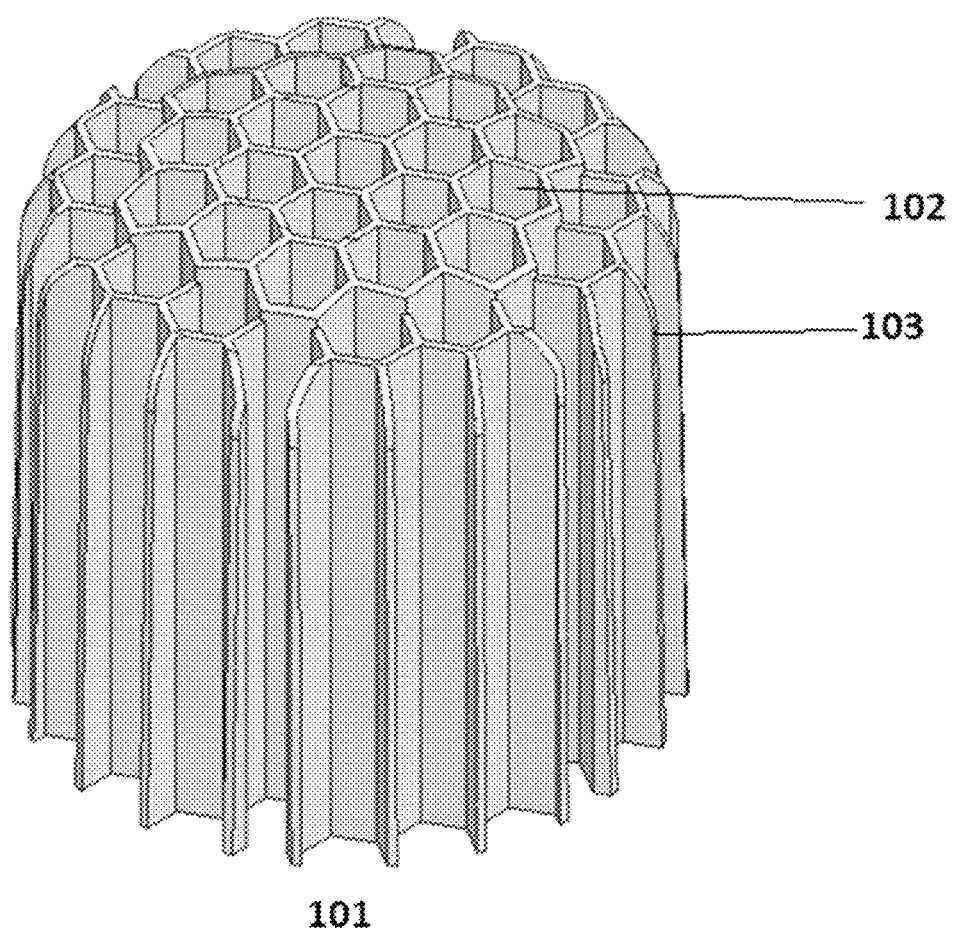
FIGS. 1A-C illustrate a flow control insert having small hexagonal flow channels.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

"Activated carbon" refers to a form of carbon processed to have small pores, increasing the surface area available for adsorption.

"Alumina" refers to aluminum oxide, $Al_2O_3$.

An "anion exchange material" is a sorbent material that removes anions from solution, replacing the removed anions with different anions.

A "cation exchange material" is a sorbent material that removes cations from solution, replacing the removed cations with different cations.

A "compression insert" is a component that can be deformed, wherein the component holds in place one or more other components when a force is applied.

The term "comprising" includes, but is not limited to, whatever follows the word "comprising." Use of the term indicates the listed elements are required or mandatory but that other elements are optional and may be present.

The term "concentric cylinders" refers to two or more cylinders having the same center point.

The term "connector" refers to a conduit or component allowing for the passage of fluid or gas.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts, or features that do not affect the basic operation of the apparatus, structure or method described.

The term "contact" refers to two or more components physically touching each other.

A "cylinder" is a three-dimensional shape having two circular ends with substantially the same diameter.

The term "dialysate flow path" refers to a pathway through which dialysate travels during dialysis therapy.

The term "dialysate pump" refers to a component that can move fluid through a dialysate flow path by applying suction or pressure.

The term "dialyzer" refers to a cartridge or container with two flow paths separated by semi-permeable membranes. One flow path is for blood and one flow path is for dialysate. The membranes can be in hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

The term "dialyzer inlet" refers to a connector through which fluid can enter a dialyzer.

The term "dialyzer outlet" refers to a connector through which fluid can exit a dialyzer.

The term "dome-shaped" refers to a top portion of a component that is rounded, with the top portion being higher at the center than around the edges.

A "flow channel" is a conduit or pathway through a flow control insert through which fluid can travel.

A "flow control insert" is a component inside of a sorbent cartridge that directs the flow of fluid through the sorbent cartridge.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type. Notably, the components that are fluidly connectable, need not be a part of a structure. For example, an outlet "fluidly connectable" to a pump does not require the pump, but merely that the outlet has the features necessary for fluid connection to the pump.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can form a "fluidly connected" state. The two points can be within or between any one or more of compartments, modules, systems, components, all of any type.

The term "glass" refers to a mixture of silicates forming a hard material.

The term "hexagonal" or a "hexagonal shape" refers to a two-dimensional shape having six sides.

The term "inner top" refers to the top portion of a container or component inside of the container or component.

"Plastic" refers to a class of synthetic materials made from organic polymers.

The term "plurality" can mean any one or more of a component or a thing.

The term "polyethylene" refers to a synthetic polymer of ethylene.

The term "polypropylene" refers to a synthetic polymer of propylene.

The terms "sorbent cartridge" and "sorbent container" can refer to a cartridge containing one or more sorbent materials for removing specific solutes from solution, such as urea. The term "sorbent cartridge" does not require the contents in the cartridge be sorbent based, and the contents of the sorbent cartridge can be any contents that can remove waste products from a dialysate. The sorbent cartridge may include any suitable amount of one or more sorbent materials. In certain instances, the term "sorbent cartridge" can refer to a cartridge which includes one or more sorbent materials in addition to one or more other materials capable of removing waste products from dialysate. "Sorbent cartridge" can include configurations where at least some materials in the cartridge do not act by mechanisms of adsorption or absorption. In any embodiment, a system may include a number of separate cartridges which can be physically separated or interconnected wherein such cartridges can be optionally detached and reattached as desired.

The term "sorbent cartridge casing" refers to the walls forming a sorbent cartridge inside which sorbent material is placed.

"Sorbent materials" are materials capable of removing specific solutes from solution, such as cations or anions.

A "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

"Stainless steel" refers to steel containing chromium and is resistant to rusting.

The term "substantially flat" refers to a surface or layer of a component wherein the top of the surface or layer is at essentially the same elevation when the component is positioned for normal use.

The term "top portion" refers to a part of a component that is intended to be at a higher elevation when the component is positioned for normal use.

"Urease" is an enzyme that converts urea to ammonium ions and carbon dioxide.

"Zirconium oxide" is a sorbent material that removes anions from a fluid, exchanging the removed anions for different anions. Zirconium oxide can also be formed as hydrous zirconium oxide.

"Zirconium phosphate" is a sorbent material that removes cations from a fluid, exchanging the removed cations for different cations.

Sorbent Cartridge Design

Figure 1B:
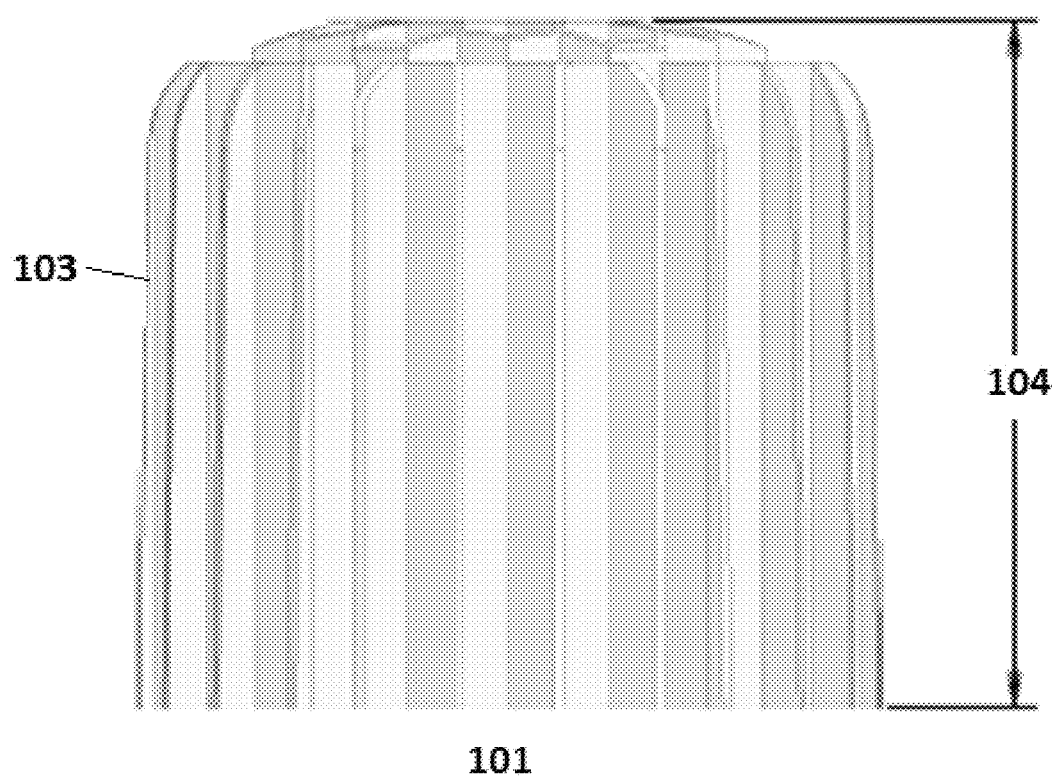
Figure 1C:
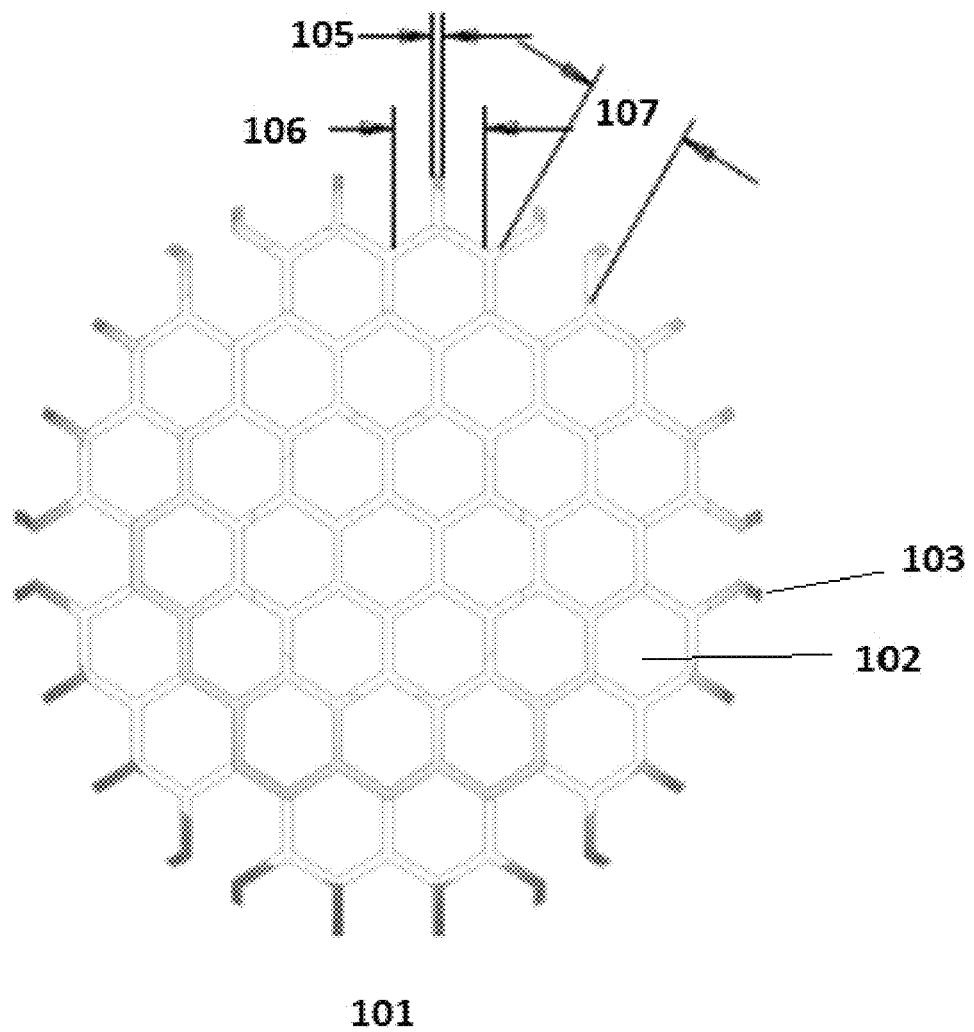

FIGS. 1A-C illustrate a flow control insert 101 for a sorbent cartridge resulting in improved flow distribution through the sorbent cartridge and more efficient removal of solutes from dialysate. FIG. 1A is a perspective view of the flow control insert 101, FIG. 1B is a side view of the flow control insert 101 and FIG. 1C is a schematic of a top view of the flow control insert 101. The flow control insert 101 can fit into a casing of a sorbent cartridge (not shown). During use, spent dialysate can travel through the sorbent cartridge, and the flow control insert will improve fluid flow distribution through the sorbent cartridge.

As illustrated in FIG. 1A, the flow control insert 101 includes a plurality of flow channels 102. For clarity, only one of the flow channels is labeled 102. In certain embodiments, as illustrated in FIG. 1A, each of the flow channels 102 can have a substantially hexagonal shape, forming a honey-comb type structure. The hexagonal shape of the flow channels 102 mimics a cylinder, which provides better flow distribution than many other shapes while minimizing space inside the sorbent cartridge lost to the flow control insert 101. The flow control insert 101 can contact an inside of a sorbent cartridge casing at ends 103. The flow control insert 101 can be held in place by a friction fit between the ends 103 and the sorbent cartridge casing, as well as by the addition of sorbent material and a seal between the top of the sorbent cartridge casing and the sorbent material. In certain embodiments, a foam compression insert can be included between the top portion of the flow control insert and an inner top of the sorbent cartridge casing to form a compression fit when the foam compression insert is compressed. The sorbent cartridge having the flow control insert 101 can contain any type of sorbent material. As a non-limiting example, the sorbent cartridge can contain a cation exchange material, such as zirconium phosphate, for removal of cations. The sorbent cartridge can also contain an anion exchange material, such as zirconium oxide, for removal of anions. Additional materials can include urease for conversion of urea to ammonium ions, alumina for use as a urease support, and/or activated carbon for removal of non-ionic solutes. Other ion exchange resins or materials can be used. The sorbent cartridge can contain any one or more sorbent materials, either arranged as discrete layers in the sorbent cartridge or mixed together.

As illustrated in in FIG. 1B, in certain embodiments, the flow control insert 101 can have a dome-shaped top. However, as described, the flow control insert 101 can alternatively have a substantially flat top portion. The height of the flow control insert 101, shown as distance 104, can be varied depending on the size of the sorbent cartridge to be used. In certain embodiments, the flow control insert 101 can be used with a filter pad or other component between the flow control insert 101 and the top and/or bottom of the sorbent cartridge. If a filter pad or other component is to be placed between the flow control insert 101 and the top and/or bottom of the sorbent cartridge, the height of the flow control insert 101 can be smaller than the height of the sorbent cartridge.

As illustrated in FIG. 1C, the diameter 107 of each hexagon flow channel 102 can be a function of the diameter of the flow control insert 101 and the number of hexagonal flow channels 102 included. One of skill in the art will be able to calculate the diameter 107, as well as the distance 106 between each point, based on the number of hexagonal flow channels 102 included and the diameter of the flow control insert 101. The width 105 of the solid portions of flow control insert 101 can be minimized to reduce the volume of space taken up by the flow control insert 101 inside the sorbent cartridge. However, the width 105 should be thick enough to provide stability to the flow control insert 101. The width 105 can be varied according to the needs of the system or user and the materials used, and can range from about 0.1 mm to about 4 mm. In certain embodiments, the width 105 can be about 2 mm.

The flow control insert 101 can be made from any material that is stable to the conditions in which the sorbent cartridge is to be used. Polypropylene, polyethylene, stainless steel, glass, or other plastics can be used.

Figure 2A:
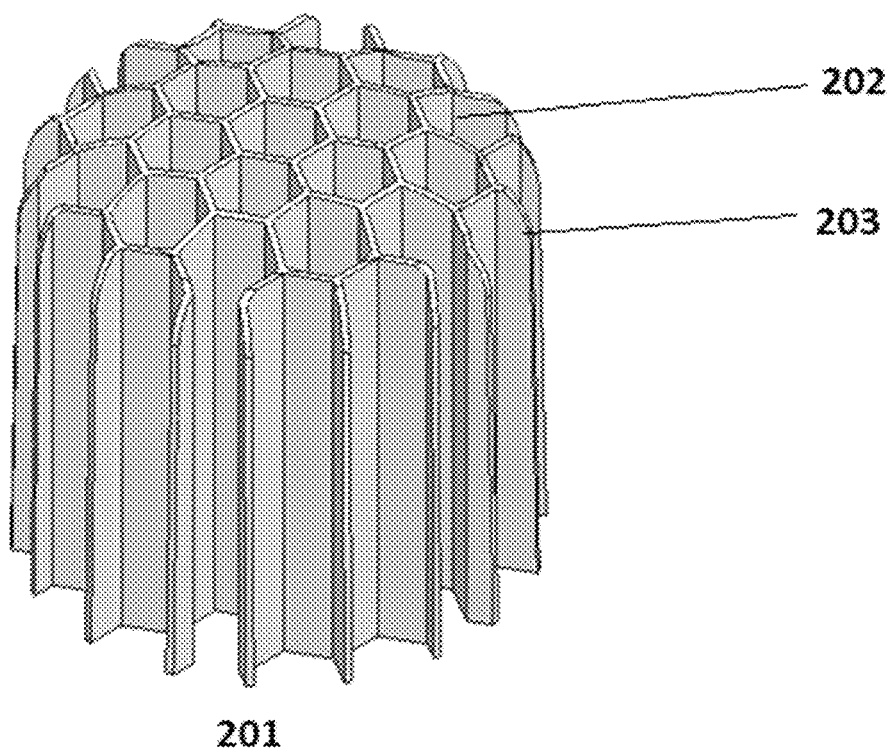
FIGS. 2A-C illustrate a flow control insert having larger hexagonal flow channels.
Figure 2B:
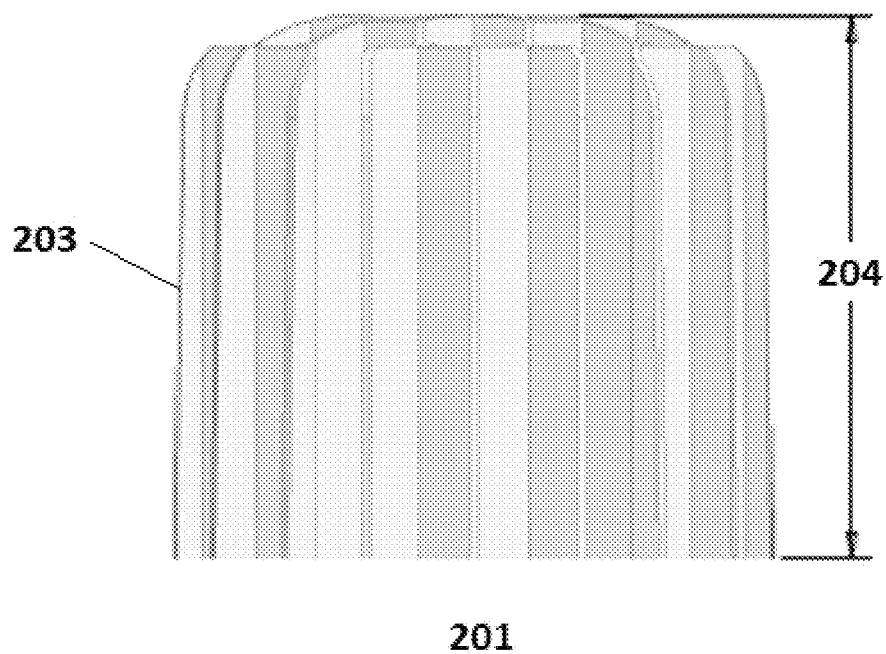
Figure 2C:
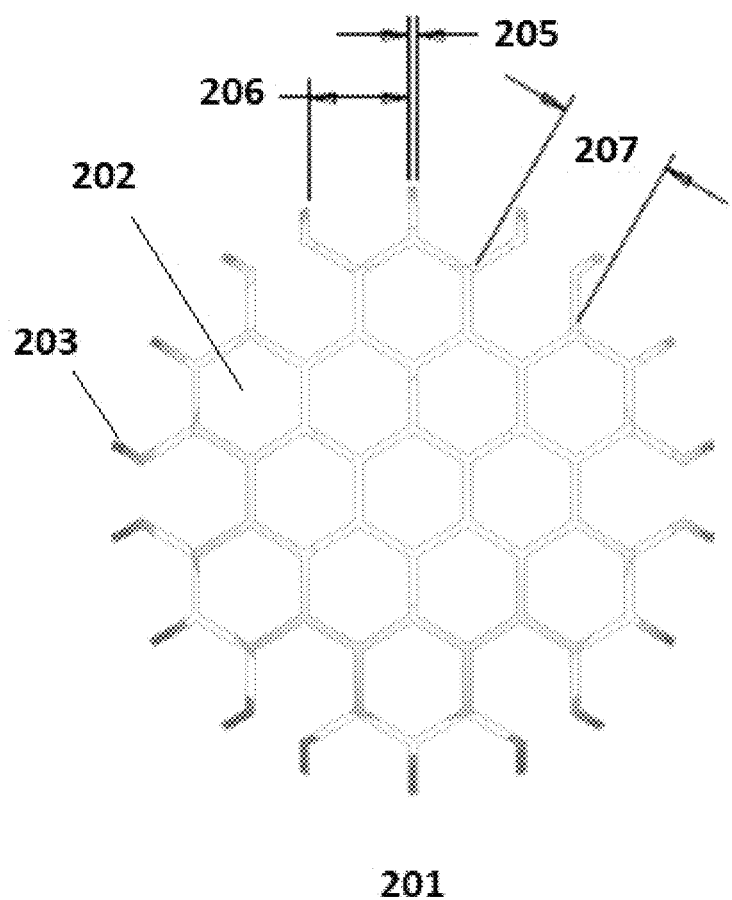

FIGS. 2A-C illustrate a flow control insert 201 having larger hexagonal flow channels 202 than those illustrated in FIGS. 1A-C. FIG. 2A is a perspective view of the flow control insert 201, FIG. 2B is a side view of the flow control insert 201 and FIG. 2C is a schematic of a top view of the flow control insert 201.

As illustrated in FIG. 2A, the flow control insert 201 includes a plurality of hexagonal flow channels 202, only one of which is labeled in FIGS. 2A-C. The flow control insert 201 can contact an inside of a sorbent cartridge casing at ends 203. The larger flow channels 202 as compared to those in FIGS. 1A-C, result in a smaller volume for the flow control insert 201 and therefore a lower size requirement for the sorbent cartridge. However, the larger flow channels 202 result in a slightly less effective flow control insert 201 at distributing flow throughout the sorbent cartridge.

As illustrated in in FIG. 2B, similar to the flow control insert of FIGS. 1A-C, the flow control insert 201 can have a dome-shaped top portion. However, as described, any described flow control insert 201 can alternatively have a substantially flat top portion. The height of the flow control insert 201, shown as distance 204, can be varied depending on the size of the sorbent cartridge to be used and is not dependent on the size of each flow channel 202.

As illustrated in FIG. 2C, the diameter 207 of each hexagon flow channel 202 depends on the diameter of the flow control insert 201 and the number of hexagonal flow channels 202 included. As such, the diameter 207 of each flow channel 202 is larger than the diameters used in the flow control insert of FIGS. 1A-C. One of skill in the art will be able to calculate the diameter 207, as well as the distance 206 between each point, based on the number of hexagonal flow channels 202 included and the diameter of the flow control insert 201. The width 205 of the solid portions of flow control insert 201 does not depend on the number of flow channels 202, and can be the same as described with reference to FIGS. 1A-C.

Figure 3A:
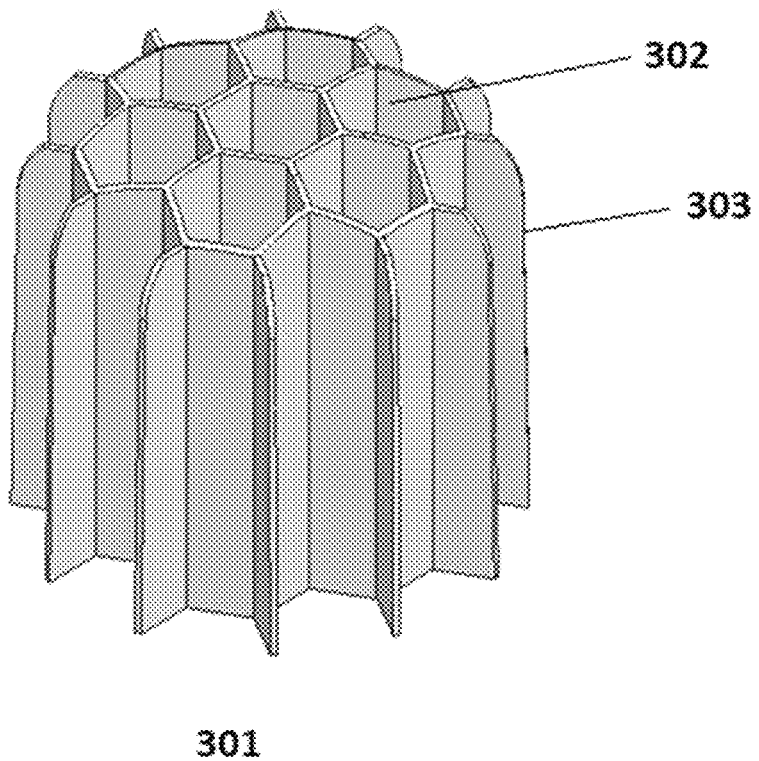
FIGS. 3A-C illustrate a flow control insert having medium sized hexagonal flow channels.
Figure 3B:
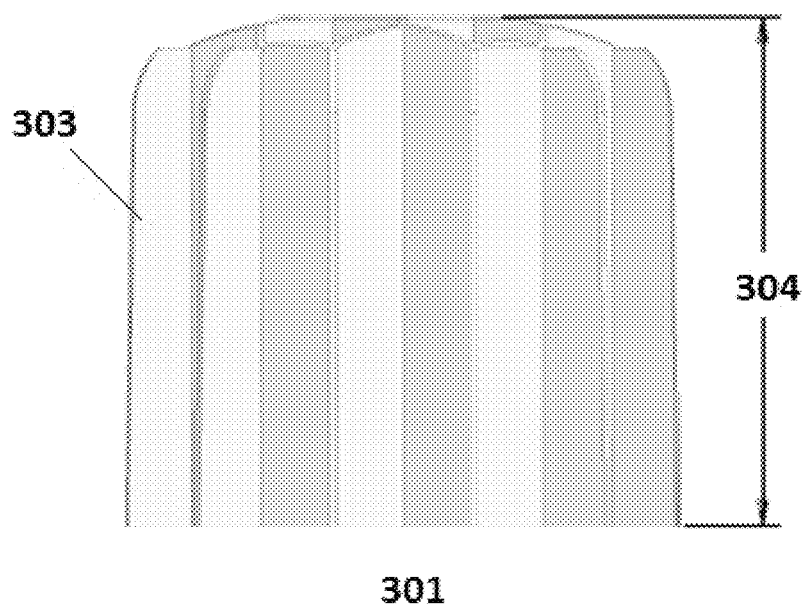
Figure 3C:
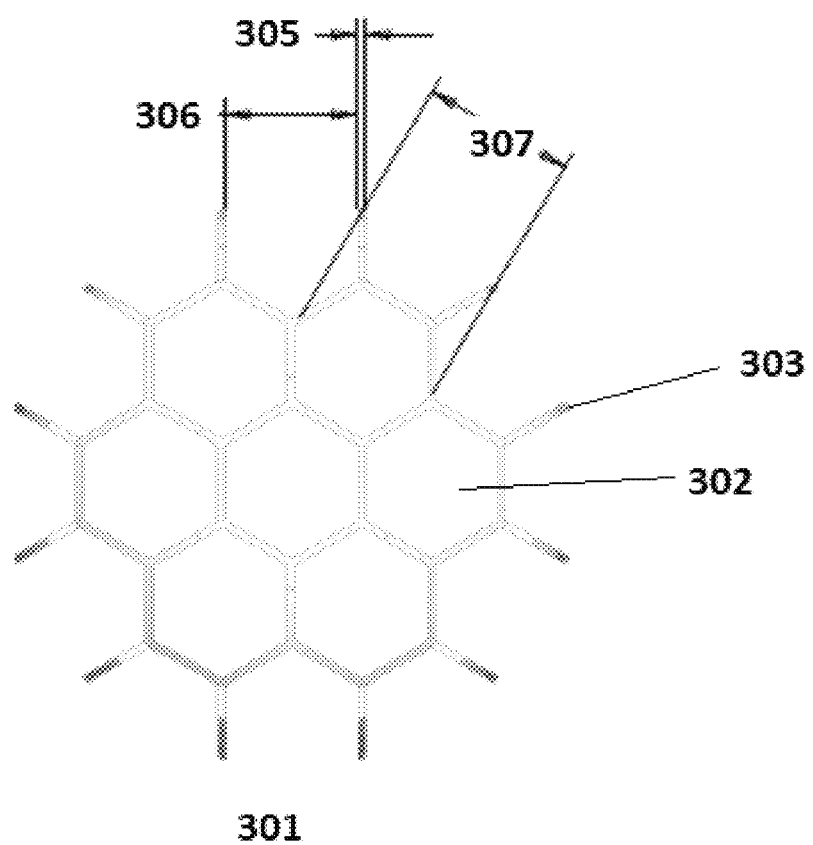

FIGS. 3A-C illustrate a flow control insert 301 having still larger flow channels 302. FIG. 3A is a perspective view of the flow control insert 301, FIG. 3B is a side view of the flow control insert 301 and FIG. 3C is a schematic of a top view of the flow control insert 301. Similar to the flow control inserts of FIGS. 1-2, the flow control insert 301 of FIG. 3A can contact an inside of a sorbent cartridge casing at ends 303. The larger flow channels 302, result in fewer total flow channels 302, and a smaller volume for the flow control insert 301 and therefore a lower size requirement for the sorbent cartridge. As illustrated in in FIG. 3B, similar to the flow control inserts of FIGS. 1-2, the flow control insert 301 can have a dome-shaped top portion. However, as described, any described flow control insert 301 can alternatively have a substantially flat top portion. The height of the flow control insert 301, shown as distance 304, can be varied depending on the size of the sorbent cartridge to be used and is not dependent on the size of each flow channel 302. For example, if the inner portion of the sorbent cartridge is 135 mm high, the flow control insert can be between 30 mm and 135 mm in length or between 20% to 100% of the total inner portion height of the sorbent cartridge. Leaving a space, between 0% to 20% of the total inner portion height of the sorbent cartridge, at the top and/or the bottom of the sorbent cartridge may improve flow through the flow control insert 301 in either flow direction, improving the ability to recharge the sorbent material in the sorbent cartridge without removing the flow control insert 301.

As illustrated in FIG. 3C, the diameter 307 of each hexagon flow channel 302 is larger than that illustrated in FIGS. 1-2. One of skill in the art will be able to calculate the diameter 307, as well as the distance 306 between each point, based on the number of hexagonal flow channels 302 included and the diameter of the flow control insert 301. The width 305 of the solid portions of flow control insert 301 does not depend on the number of flow channels 302.

Figure 4A:
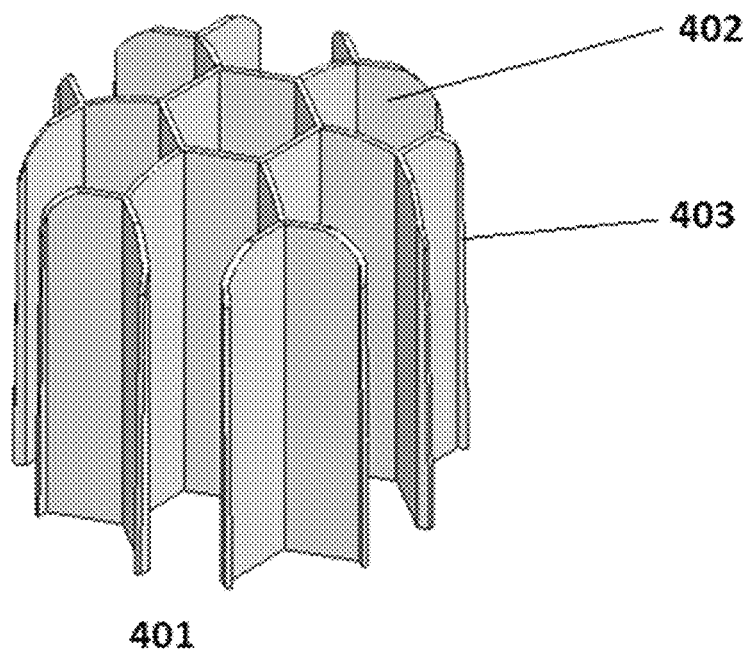
FIGS. 4A-C illustrate a flow control insert having large sized hexagonal flow channels.
Figure 4B:
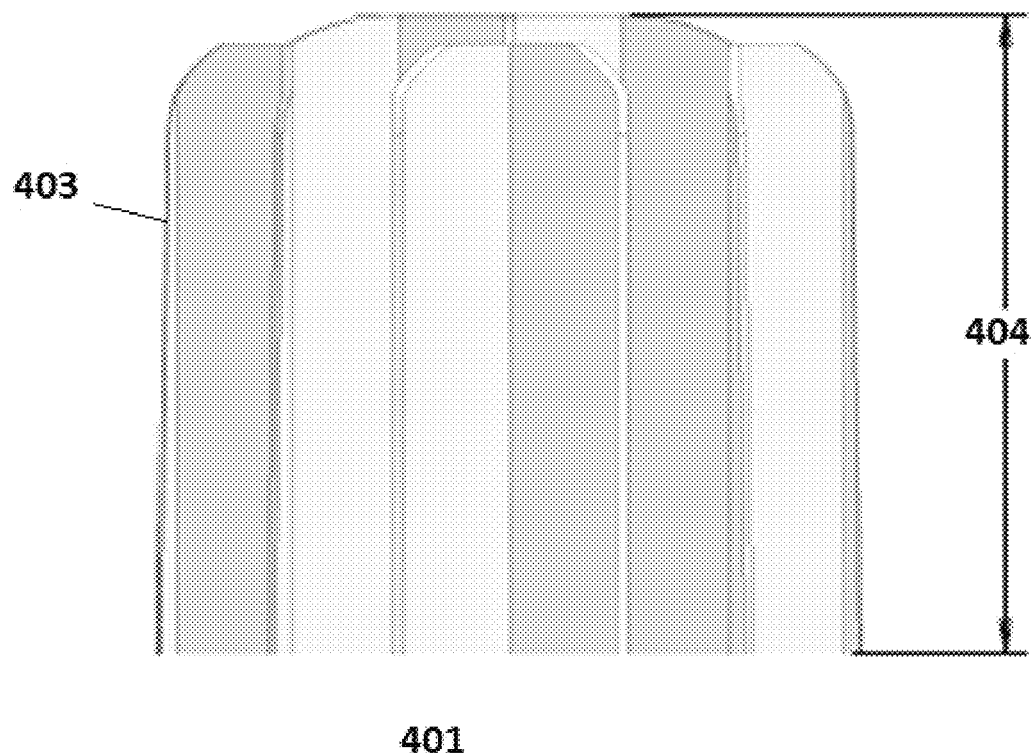
Figure 4C:
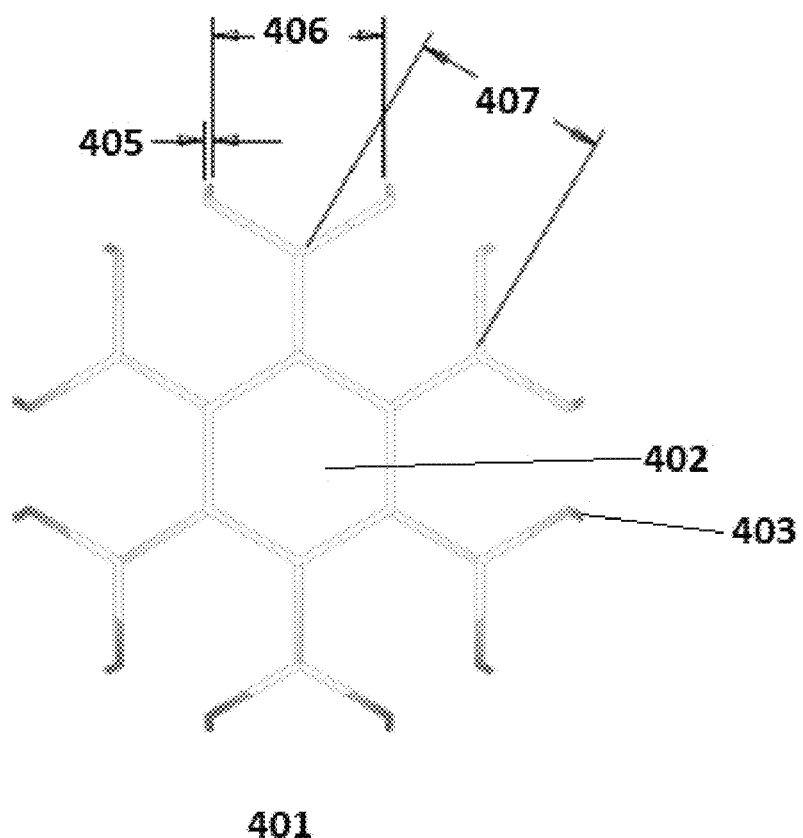

FIGS. 4A-C illustrate a flow control insert 401 having 7 flow channels 402. FIG. 4A is a perspective view of the flow control insert 401, FIG. 4B is a side view of the flow control insert 401 and FIG. 4C is a schematic of a top view of the flow control insert 401. As illustrated in FIG. 3A, the flow control insert 401 can contact an inside of a sorbent cartridge casing at ends 403, forming six of the seven total flow channels 402. As illustrated in in FIG. 4B, similar to the flow control inserts of FIGS. 1-3, the flow control insert 401 can have a dome-shaped top. The height of the flow control insert 401, shown as distance 404, depends on the size of the sorbent cartridge to be used and is not dependent on the size of each flow channel 402. The diameter 407 of each hexagon flow channel 402 as well as the distance 406 between each point larger than that illustrated in FIGS. 1-3. The width 405 of the solid portions of flow control insert 401 can be set based on the needs of the user for stability, durability and to minimize volume of the flow control insert 401.

FIGS. 1-4 each illustrate flow control inserts having hexagonal flow channels with varying sizes. In certain embodiments, the diameters of the flow channels can be between 10 mm to 60 mm.

Figure 5A:
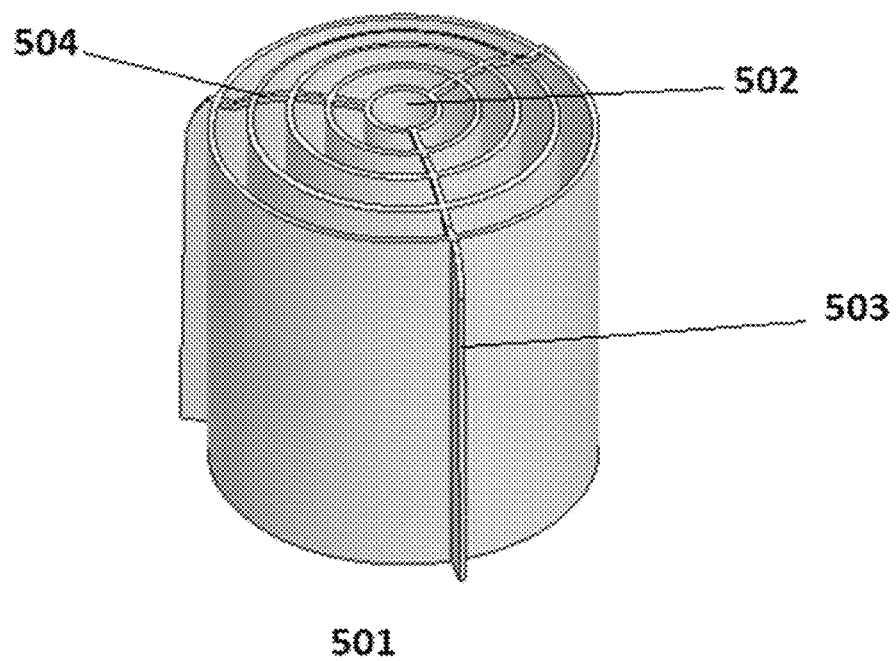
FIGS. 5A-C illustrate a flow control insert having flow channels forming concentric cylinders.
Figure 5B:
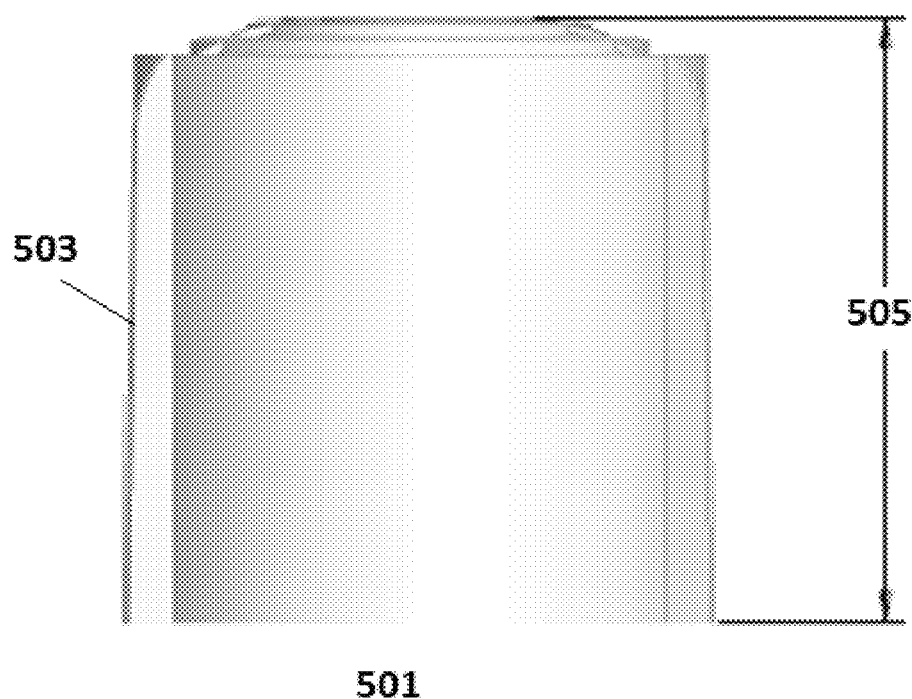
Figure 5C:
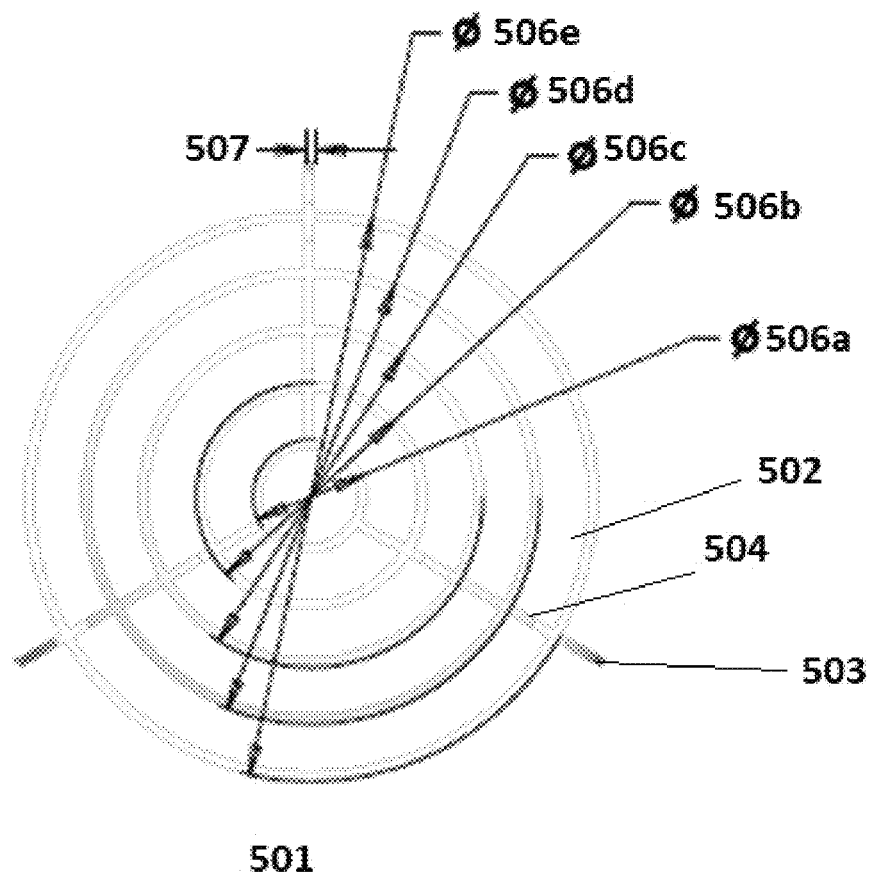

FIGS. 5A-C illustrate a flow control insert 501 having concentric cylinder flow channels 502. FIG. 5A is a perspective view of the flow control insert 101, FIG. 5B is a side view of the flow control insert 501 and FIG. 5C is a schematic of a top view of the flow control insert 501. Similar to the hexagonal flow channel inserts of FIGS. 1-4, the flow control insert 501 of FIGS. 5A-C can fit within a sorbent cartridge (not shown). Concentric cylinders mimic cylindrical flow, improving flow distribution through the sorbent cartridge, similar to the hexagon shaped flow channels illustrated in FIGS. 1-4.

The flow control insert 501 illustrated in FIG. 5A has six concentric flow channels 502, only one of which is labeled for clarity. Although illustrated with six concentric cylinder flow channels 502, the flow control insert 501 can have more or fewer flow channels 502, similar to the designs shown in FIGS. 1-4. The flow control insert 501 can contact an inside of a sorbent cartridge (not shown) casing at ends 503, which form the sixth flow channel 502 between the outside of the flow control insert 501 and the inner wall of the sorbent cartridge casing. Connectors 504 can connect the solid portions of the flow control insert 501 to prevent the concentric cylinder flow channels 502 from expanding or contracting.

As illustrated in in FIG. 5B, the flow control insert 501 can have a dome-shaped top. However, as described, the cylindrical flow control insert 501 can alternatively have a substantially flat top portion, similar to the hexagonal flow control inserts of FIGS. 1-4. The height of the flow control insert 501, shown as distance 505, does not depend on the shape of the flow channels 502 and can be set depending on the size of the sorbent cartridge to be used.

As illustrated in FIG. 5C, the width 507 of the solid portions of flow control insert 501 can be minimized to reduce the volume of space taken up by the flow control insert 501 inside the sorbent cartridge. However, similar to the flow control inserts of FIGS. 1-4, the width 507 should be thick enough to provide stability to the flow control insert 501. The width 507 can be set based on the needs of the user, similar to the flow control inserts of FIGS. 1-4. In certain embodiments, the width 507 can be about 2 mm. In FIG. 5C, 506a is the radius of the inner cylinder, 506b is the radius of the second cylinder, 506c is the radius of the third cylinder, 506d is the radius of the fourth cylinder, and 506e is the radius of the outer cylinder. As with the hexagonal flow channels of FIGS. 1-4, the number of cylindrical flow channels can be varied, and can include 2, 3, 4, 5, 6, 7, or more concentric cylinders depending on the size of the flow control insert 501, the thickness of the flow control insert 501 and the thickness of each concentric cylinder used.

Figure 6:
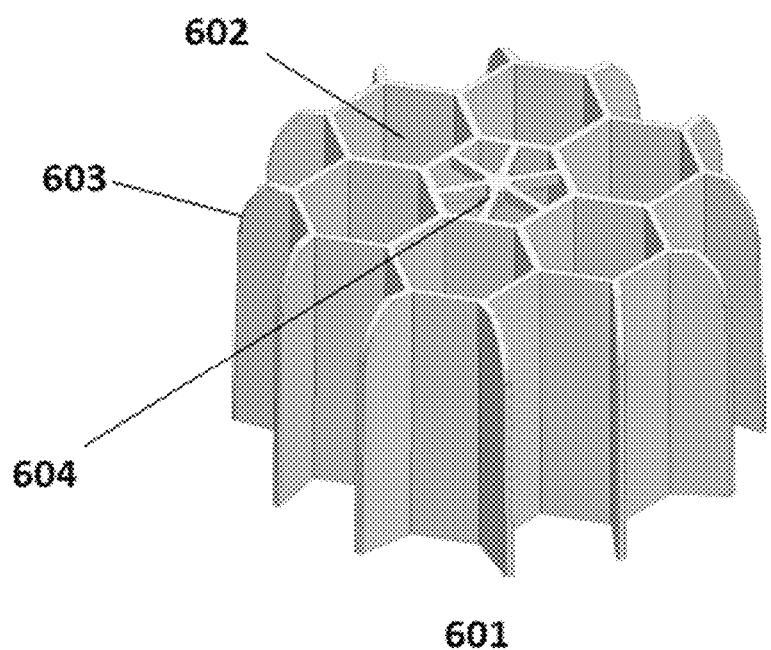
FIG. 6 illustrates a flow control insert having a substantially flat top portion.

FIG. 6 illustrates a flow control insert 601 having a substantially flat top portion. The flow control insert 601 is similar to the domed flow control insert illustrated in FIGS. 3A-C. However, any of the flow control inserts with a dome-shaped top portion illustrated in FIGS. 1-5 can be constructed with a substantially flat top portion. Similar to the other designs, the flow control insert 601 includes a plurality of flow channels 602. Although illustrated as having hexagonal flow channels 602, the flat flow control insert 601 can alternatively have concentric cylinder flow channels, similar to the design illustrated in FIGS. 5A-C. The flow control insert 601 can be placed in a sorbent cartridge (not shown), with the end portions 603 contacting the wall of the sorbent cartridge casing, forming the outer flow channels. In certain embodiments, spokes 604 can be included in the center flow channel 602 to improve stability and manufacturability.

The top of the dome-shaped flow control inserts illustrated in FIGS. 1-5 can conform to the shape of the sorbent cartridge casing, while the substantially flat flow control insert of FIG. 6 can leave a small space between the top of the flow control insert and the top of the sorbent cartridge. The additional space formed with the flat top flow control insert can improve flow distribution in the opposite direction through the sorbent cartridge, which may be useful in certain processes, such as recharging the sorbent material after use.

Other shapes for flow channels that approximate the shape of a cylinder, such as circular flow channels, can be used. In certain embodiments, the flow channels can be a set of non-concentric cylinders, as in a bundle of straws. However, the hexagonal and concentric cylinder flow channels illustrated in FIGS. 1-6 advantageously cover the entire surface of the flow control insert efficiently, allowing fluid to only travel through the flow channels without leaving excess dead space in the sorbent cartridge.

Although the hexagonal flow channels illustrated in FIGS. 1-4 and 6 are all shown as the same size, in certain embodiments the flow control inserts can have different sized flow channels. Different sized flow channels allow for the creation of unique flow distribution patterns through the sorbent cartridge. Having varying hexagon sizes with a flow control insert can result in a desired flow distribution. For example, smaller hexagons can be used towards the center of the flow control insert, with the hexagons increasing in size towards approach the sides of the sorbent cartridge. Smaller hexagons towards the center and larger hexagons towards the outside may prevent a parabolic flow pattern with faster flow at the center and slower flow towards the walls, which is common for flow through a cylinder without a flow control insert.

In certain embodiments, the flow channels can be filled with different sorbent materials. For example, certain flow channels can be filled with a first type of ion exchange resin and other flow channels can be filled with a second type of ion exchange resin to tailor solute removal from a fluid. Having different sorbent materials in different flow channels may result in specified partial solute removal. For example, if half of the hexagons are filled with cation exchange material such as zirconium phosphate and the other half of the hexagons are filled with an anion exchange material such as zirconium oxide, the sorbent cartridge would only remove half of the cations ($Ca^+$, $Mg^+$, $K^+$) and half of the anions ($PO4^-$). In some cases, it may be beneficial to remove only a portion of the phosphate or cations from a patient during dialysis. Phosphate in particular is a common ion that can be over removed during traditional dialysis that happens more than 3 times per week. It is common for phosphate to be added as an infusate in the dialysate, however, if only a portion of the flow channels have an anion exchange material, less of the phosphate will be removed, reducing the need to add additional phosphate to the dialysate. In certain embodiments, a portion of the flow channels can be kept empty to tailor a particular % removal of a solute from the dialysate.

Figure 7:
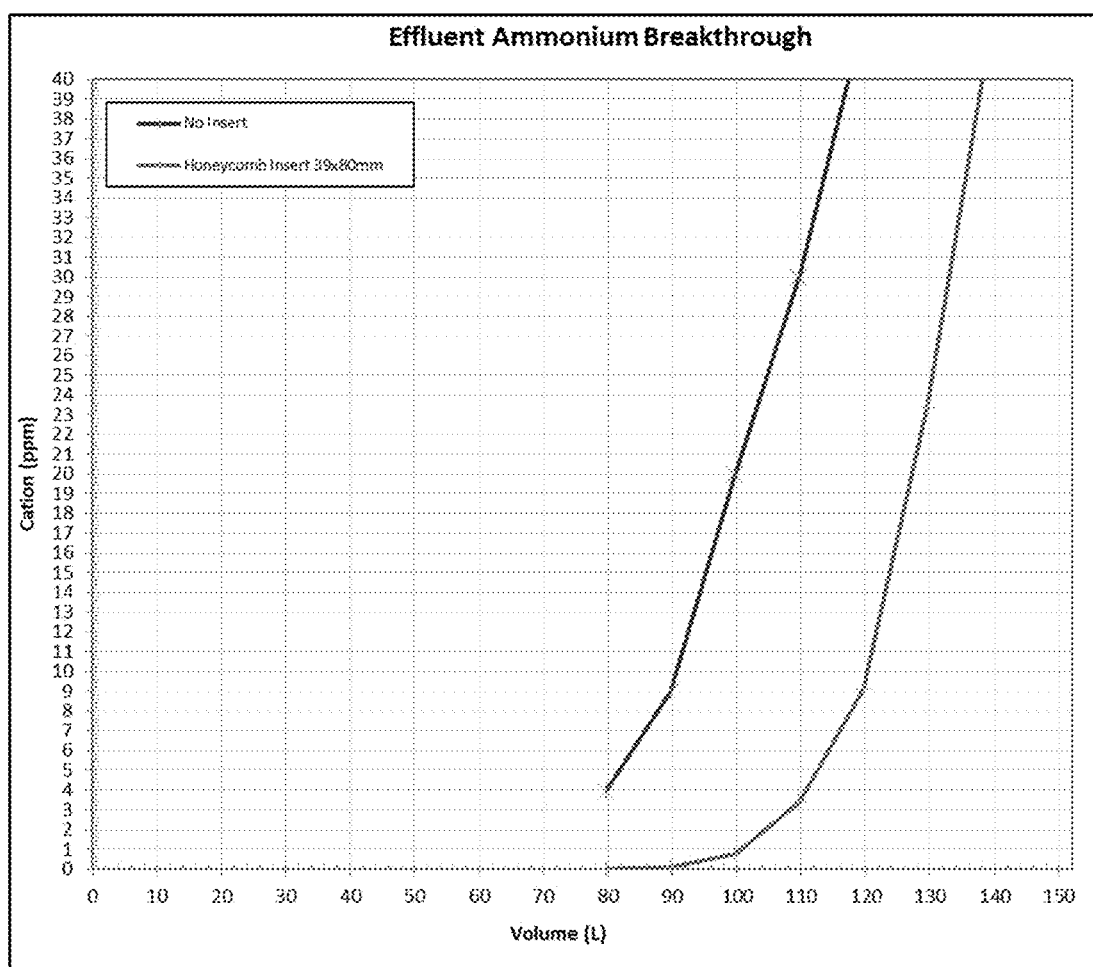
FIG. 7 is a graph showing ammonium ion concentration in sorbent cartridge effluent as a function of volume.

As described, by improving the flow distribution through the sorbent cartridge, the efficiency of solute removal by the sorbent cartridge is increased. FIG. 7 is a graph showing the volume of dialysate that can be flowed through a zirconium phosphate sorbent cartridge before breakthrough occurs. The x-axis in FIG. 7 is the volume of fluid pumped through the sorbent cartridge. The y-axis in FIG. 7 is the concentration of ammonium ions in fluid exiting the sorbent cartridge. To test the sorbent cartridges, a simulated spent dialysate feed having 130 mM Na, 36 mM, $HCO_3$, 3.2 mM K, 2 mM Ca, 1 mM Mg, 23.4 mM $NH_4$, plus other components was pumped through each sorbent cartridge at 600 ml/min at a temperature of 37° C. The higher line in FIG. 7 shows the ammonium ion concentration vs. volume for a zirconium phosphate sorbent cartridge without a flow control insert, while the lower line shows the ammonium ion concentration vs. volume for a zirconium phosphate sorbent cartridge with a flow control insert similar to that illustrated in FIG. 3A. As illustrated in FIG. 7, significant levels of ammonium ions were present in fluid exiting the sorbent cartridge without the flow control insert by the time 80 L of simulated spent dialysate was pumped through the sorbent cartridge. In contrast, when using the flow control insert, significantly more volume can be treated by the sorbent cartridge before reaching similar levels of cations in the treated fluid. Using the flow control insert, the ammonium capacity at 10 ppm increases from about 90 L without the flow control insert to about 120 L with the flow control insert, which corresponds to about a 33% in capacity.

Figure 8:
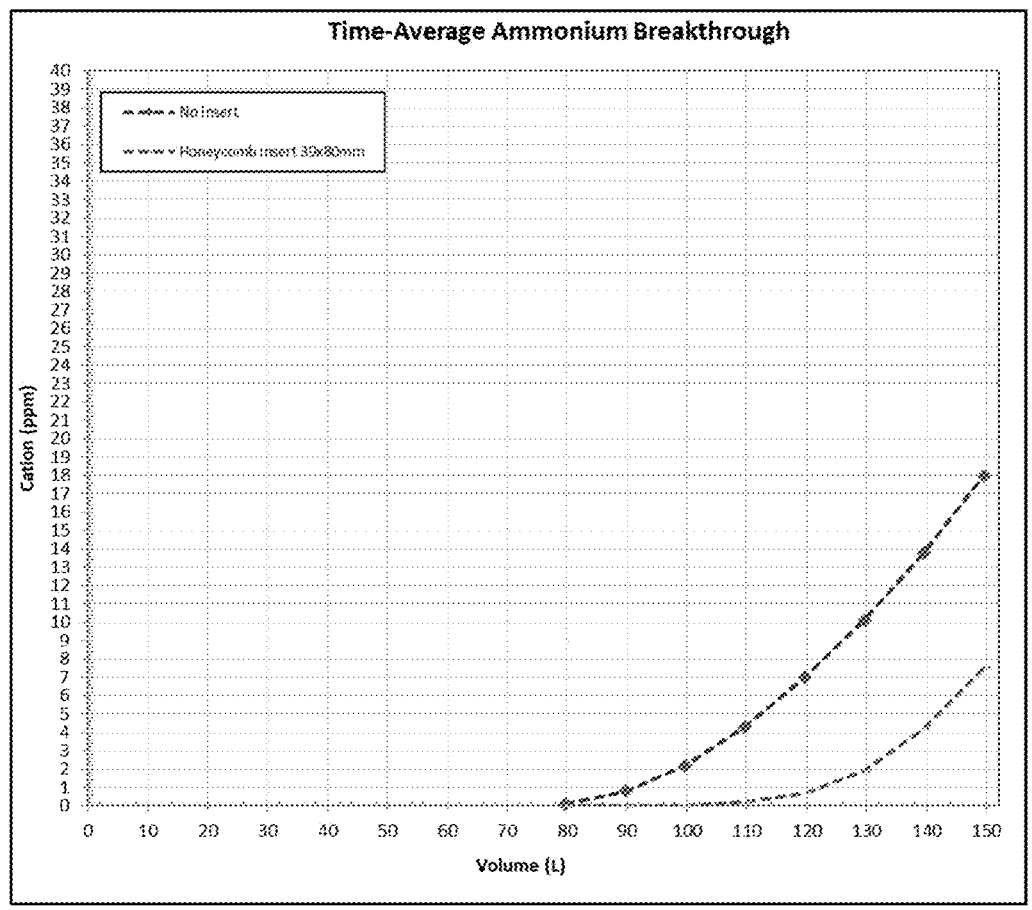
FIG. 8 is a graph showing time averaged ammonium ion concentration in sorbent cartridge effluent as a function of volume.

FIG. 8 is a graph showing the time-averaged effluent level of ammonium ions vs. volume of simulated spent dialysate passed through the cartridge. The higher line in FIG. 8 is the time averaged ammonium ion concentration vs. volume for a zirconium phosphate sorbent cartridge without a flow control insert, while the lower line shows the time averaged ammonium ion concentration vs. volume for a zirconium phosphate sorbent cartridge with a flow control insert similar to that illustrated in FIG. 3A. The simulated spent dialysate and conditions used for the data of FIG. 8 are the same as described with respect to FIG. 7. As illustrated in FIG. 8, the time-average ammonium capacity at 2-ppm increases from 100 liters without using a flow control insert to 130 liters with a flow control insert, a 30% increase.

Figure 9:
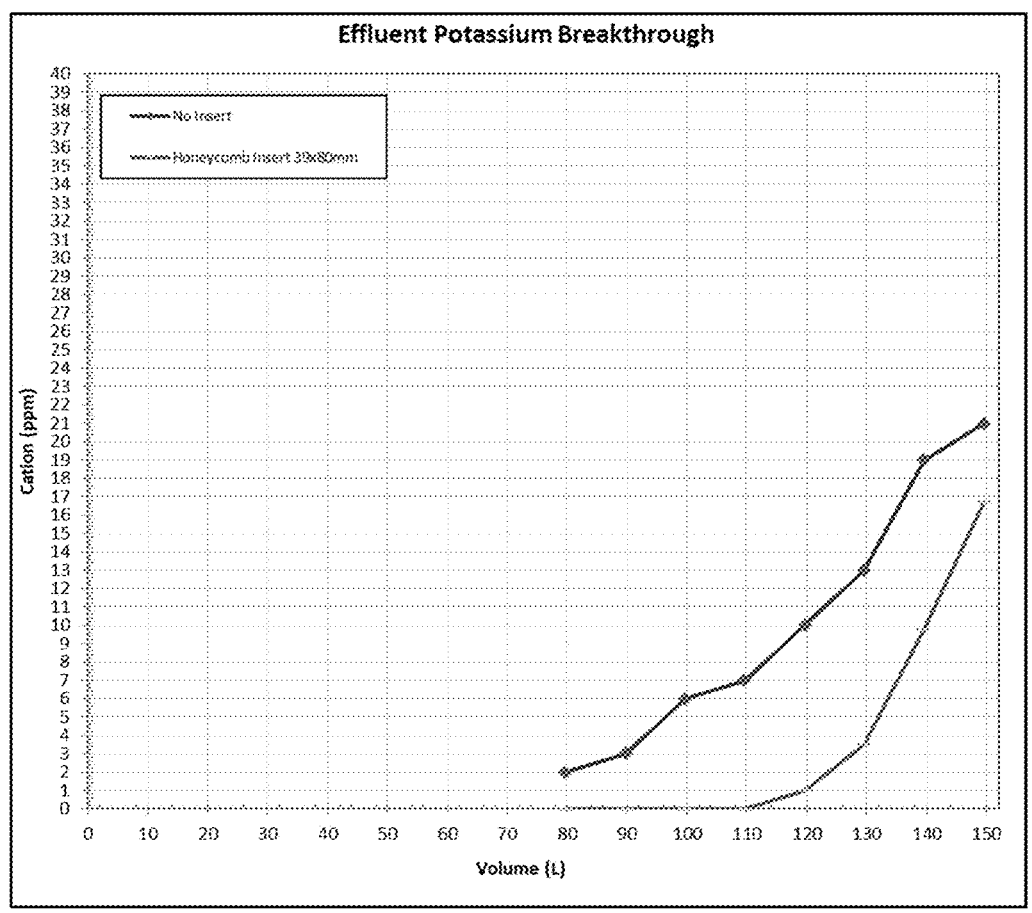
FIG. 9 is a graph showing potassium ion concentration in sorbent cartridge effluent as a function of volume.

FIG. 9 is a graph showing the instantaneous potassium concentration in fluid exiting a sorbent cartridge vs. volume of dialysate pumped through the sorbent cartridge. The data in FIG. 9 was obtained with the same conditions and materials as that in FIGS. 7-8. The higher line in FIG. 9 is the instantaneous potassium ion concentration vs. volume for a zirconium phosphate sorbent cartridge without a flow control insert, while the lower line shows the instantaneous potassium ion concentration vs. volume for a zirconium phosphate sorbent cartridge with a flow control insert similar to that illustrated in FIG. 3A. As illustrated in FIG. 9, the sorbent cartridge potassium capacity at 8-ppm increases from 112 liters without a flow control insert to 137 liters when using the flow control insert, a 22% increase.

As illustrated in the graphs of FIGS. 7-9, the flow control insert significantly increases the capacity of a sorbent cartridge by improving fluid flow distribution through the sorbent cartridge.

Figure 10:
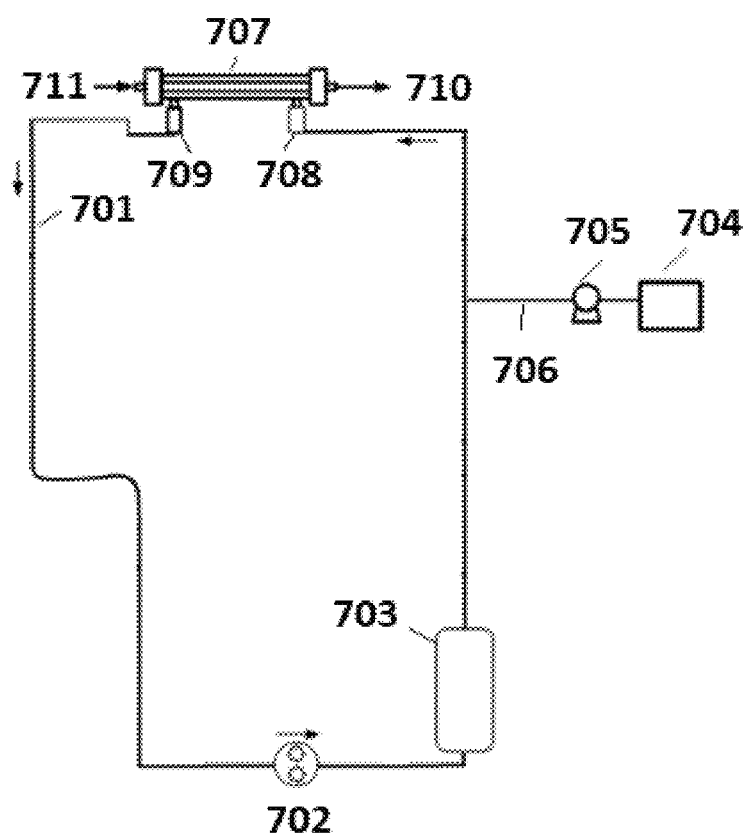
FIG. 10 is a dialysate flow path.

FIG. 10 illustrates a simplified dialysate flow path 701 for use in hemodialysis. Spent dialysate can be pumped through a dialyzer 707 from a first connector 708 fluidly connected to the inlet of the dialyzer 707 to a second connector 709 fluidly connected to an outlet of the dialyzer 707. At the same time, blood from a patient enters the dialyzer 707 through blood inlet 711 and exits through blood outlet 710. Dialysate pump 702 provides the force necessary for moving dialysate through the dialysate flow path 701. The dialysate exiting dialyzer 707 can be regenerated by passing the dialysate through a sorbent cartridge 703. As described herein, the sorbent cartridge 703 can contain a flow control insert, along with one or more sorbent materials. The sorbent materials in sorbent cartridge 703 can include zirconium phosphate for removal of cations from the dialysate, zirconium oxide for removal of anions from the dialysate, and activated carbon for removal of creatinine, glucose, uric acid, β2-microglobulin and other non-ionic toxins, except urea, from the dialysate. The sorbent cartridge can also include urease, which converts urea to ammonium ions and carbon dioxide with the ammonium ions removed by the zirconium phosphate. In certain embodiments, the urease can be immobilized on alumina to prevent the urease from escaping the sorbent cartridge. Because the zirconium phosphate will remove potassium, calcium, and magnesium from the spent dialysate, cations can be added back into the dialysate from infusate source 704. The infusate solution can be added through fluid line 706 by infusate pump 705. Although shown as a single infusate source 704 in FIG. 10, one of skill in the art will understand that the system can include any number of infusate sources. Additional components, such as a sodium source, a bicarbonate source, a water source, a degasser and any other components of a dialysis system can be added.

Although shown as a single sorbent cartridge 703 in FIG. 10, the sorbent materials can be contained within any number of sorbent modules. For example, a first sorbent module can contain activated carbon, urease, and alumina, while a second sorbent module contains zirconium phosphate, and a third sorbent module contains zirconium oxide. Each of the sorbent modules can contain a flow control insert. Separating the sorbent materials into different modules can ease recharging of the individual sorbent materials without the need to remove the sorbent materials from the sorbent cartridge. Any number of sorbent modules can be used containing any combination of sorbent materials, so long as zirconium phosphate is located downstream of any urease.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A sorbent cartridge comprising:
   a sorbent cartridge casing;
   at least one sorbent material inside the sorbent casing; and
   a flow control insert; the flow control insert comprising a plurality of flow channels filled with the at least one sorbent material;
   the plurality of flow channels extending within the sorbent cartridge casing from an inlet of the sorbent cartridge casing towards an outlet of the sorbent cartridge casing; and
   wherein the flow control insert is configured to distribute fluid flow more efficiently throughout the sorbent material to increase the adsorptive capacity of the sorbent cartridge.

2. The sorbent cartridge of claim 1, wherein the at least one sorbent material comprises zirconium phosphate.

3. The sorbent cartridge of claim 1, wherein the at least one sorbent material comprises zirconium oxide.

4. The sorbent cartridge of claim 1, wherein the at least one sorbent material comprises at least one sorbent material selected from a group consisting of activated carbon, alumina, urease, zirconium phosphate, zirconium oxide, an anion exchange material, and a cation exchange material.

5. The sorbent cartridge of claim 1, wherein each of the plurality of flow channels has a hexagonal shape.

6. The sorbent cartridge of claim 1, wherein the plurality of flow channels form a plurality of cylinders wherein each cylinder houses a portion of the plurality of flow channels filled with the at least one sorbent material.

7. The sorbent cartridge of claim 6, wherein the plurality of cylinders is a plurality of concentric cylinders.

8. The sorbent cartridge of claim 1, wherein the flow control insert has a substantially flat top portion.

9. The sorbent cartridge of claim 1, wherein the flow control insert has a dome-shaped top portion.

10. The sorbent cartridge of claim 1, further comprising a compression insert between a top portion of the flow control insert and an inner top of the sorbent cartridge casing.

11. The sorbent cartridge of claim 10, wherein the flow control insert contacts the compression insert.

12. A flow control insert for a sorbent cartridge, comprising:
    a plurality of flow channels;
    the flow control insert insertable into the sorbent cartridge containing at least one sorbent material;
    the plurality of flow channels extending within the sorbent cartridge from an inlet of the sorbent cartridge towards an outlet of the sorbent cartridge;
    wherein the at least one sorbent material is within the plurality of flow channels wherein the flow control insert is configured to distribute fluid flow more efficiently throughout the sorbent material to increase the adsorptive capacity of the sorbent cartridge.

13. The flow control insert of claim 12, wherein each of the plurality of flow channels has a substantially hexagon shape.

14. The flow control insert of claim 12, wherein the plurality of flow channels form a plurality of cylinders wherein each cylinder houses a portion of the plurality of flow channels filled with the at least one sorbent material.

15. The flow control insert of claim 14, wherein the plurality of cylinders is a plurality of concentric cylinders.

16. The flow control insert of claim 12, wherein the flow control insert has a substantially flat top portion.

17. The flow control insert of claim 12, wherein the flow control insert has a dome-shaped top portion.

18. The flow control insert of claim 12, wherein the flow control insert is constructed from a material selected from: polypropylene, polyethylene, stainless steel, glass, plastic, or a combination thereof.

19. A dialysate flow path, comprising:
a first connector fluidly connectable to a dialyzer outlet;
a second connector fluidly connectable to a dialyzer inlet;
at least one dialysate pump; and
at least a first sorbent module; the sorbent module comprising:
a sorbent cartridge casing;
at least one sorbent material inside the sorbent casing; and
a flow control insert; the flow control insert comprising a plurality of flow channels filled with the at least one sorbent material; the plurality of flow channels extending within the sorbent cartridge casing from an inlet of the sorbent cartridge casing towards an outlet of the sorbent cartridge casing wherein the flow control insert is configured to distribute fluid flow more efficiently throughout the sorbent material to increase the adsorptive capacity of the sorbent cartridge.

20. The dialysate flow path of claim 19, further comprising at least a second sorbent module; wherein the second sorbent module comprises a second sorbent cartridge casing; at least one sorbent material inside the second sorbent cartridge casing; and a second flow control insert; the second flow control insert comprising a plurality of flow channels filled with the at least one sorbent material; the plurality of flow channels of the second flow control insert extending within the second sorbent cartridge casing from an inlet of the second sorbent cartridge casing towards an outlet of the second sorbent cartridge casing.

* * * * *